United States Patent
Dai

(10) Patent No.: US 9,334,248 B2
(45) Date of Patent: May 10, 2016

(54) SYNTHETIC METHOD FOR THE PREPARATION OF 1,2-BENZISOTHIAZOLIN-3-ONE

(71) Applicant: Shouguang Syntech Fine Chemical Co., Ltd., Yangkou Town (CN)

(72) Inventor: Mingben Dai, Yangkou Town (CN)

(73) Assignee: Shouguang Syntech Fine Chemical Co., Ltd. (CN)

( * ) Notice: Subject to any disclaimer, the term of this patent is extended or adjusted under 35 U.S.C. 154(b) by 0 days.

(21) Appl. No.: 14/719,825

(22) Filed: May 22, 2015

(65) Prior Publication Data

US 2015/0336910 A1 Nov. 26, 2015

Related U.S. Application Data

(60) Provisional application No. 62/039,442, filed on Aug. 20, 2014.

(51) Int. Cl.
*C07D 275/04* (2006.01)

(52) U.S. Cl.
CPC .................................. *C07D 275/04* (2013.01)

(58) Field of Classification Search
USPC ........................................................ 548/209
See application file for complete search history.

(56) References Cited

U.S. PATENT DOCUMENTS

| 4,736,040 A | 4/1988 | Tonne et al. |
|---|---|---|
| 8,802,862 B2 | 8/2014 | Hiyama et al. |
| 2013/0345434 A1* | 12/2013 | Kanda et al. .................. 548/209 |

FOREIGN PATENT DOCUMENTS

| CN | 102491955 A | 6/2012 |
|---|---|---|
| CN | 103130738 A | 6/2013 |
| CN | 103145638 A | 6/2013 |
| CN | 103429579 A | 12/2013 |
| CN | 103965132 | 9/2014 |
| EP | 0702008 A2 | 3/1996 |
| EP | 2687519 A1 | 1/2014 |
| EP | 2687520 A1 | 1/2014 |
| JP | 2002088072 A | 3/2002 |
| JP | 2013043881 A | 3/2013 |
| JP | 2013043882 A | 3/2013 |
| WO | WO-2012/127996 A1 * | 9/2012 |

OTHER PUBLICATIONS

Chemical Abstracts Registry No. 110502-29-9, indexed in the Registry file on STN CAS Online Oct. 3, 1987.*
Chemical Abstracts Registry No. 1160509-17-0, indexed in the Registry file on STN CAS Online Jun. 30, 2009.*
Chemical Abstracts Registry No. 859791-22-3, indexed in the Registry file on STN CAS Online Aug. 12, 2005.*
Node et al., Tetrahedron Letters, 42, 2001, pp. 9207-9210.*
Butanethiol, ChemSpider, date not available.*
Pentanethiol, ChemSpider, date not available.*
Hexanethiol, ChemSpider, date not available.*
European Search Report for EP 14181603.3-1452 mailed Oct. 10, 2014.

* cited by examiner

*Primary Examiner* — Laura L. Stockton
(74) *Attorney, Agent, or Firm* — Drinker Biddle & Reath LLP

(57) ABSTRACT

The present invention relates to a method for producing a 1,2-benzisothiazolin-3-one compound (I) by reacting a 2-halobenzonitrile compound (II) with a thiol compound (III) to form an intermediate (IV) and subsequently reacting the intermediate (IV) with a halogenation agent in the presence of water to form a reaction mixture (RM), comprising the 1,2-benzisothiazolin-3-one compound (I) and a halide compound (V).

13 Claims, No Drawings

SYNTHETIC METHOD FOR THE PREPARATION OF 1, 2-BENZISOTHIAZOLIN-3-ONE

This patent application claims the benefit of U.S. provisional patent application Ser. No. U.S. 62/039,442, filed on Aug. 20, 2014 and CN patent application Ser. No. CN 103965132, filed on May 26, 2014, incorporated in their entirety herein by reference.

The present invention relates to a method for producing a 1,2-benzisothiazolin-3-one compound (I) by reacting a 2-halobenzonitrile compound (II) with a thiol compound (III) to form an intermediate (IV) and subsequently reacting the intermediate (IV) with a halogenation agent in the presence of water to form a reaction mixture (RM), comprising the 1,2-benzisothiazolin-3-one compound (I) and a halide compound (V).

1,2-benzisothiazolin-3-one compounds (I), especially 1,2-benzisothiazolin-3-one (BIT) itself, are of high industrial relevance as they are high efficient fungicides. Furthermore, 1,2-benzisothiazolin-3-one compounds (I) inhibit the growth of microorganisms like bacteria, fungi, mold and mildew. 1,2-benzisothiazolin-3-one compounds (I) are typically used as a preservative in emulsion paints, varnishes, adhesives, washing agents and paper pulps.

Various methods for the production of 1,2-benzisothiazolin-3-ones are described in the state of the art.

For example, U.S. Pat. No. 4,736,040 describes a method for the preparation of 1,2-benzisothiazolin-3-ones by reacting 2,2'-dithiobenzamides with an oxygenation agent in the presence of an aqueous alkaline medium. The 2,2'-dithiobenzamides are prepared by nitrosation of anthranilamides and subsequently reacting the thus obtained product with sulfur dioxide in the presence of a catalyst. This method for the preparation of 1,2-benzisothiazolin-3-ones is both, time-consuming and costly as many reaction steps are necessary.

A more simple method for the preparation of 1,2-benzisothiazolin-3-ones is described in EP 2 687 519. In the method according to EP 2 687 519 first a 2-halobenzonitrile is reacted with an alkylthiol having from 1 to 4 carbon atoms to give a 2-(alkylthio)benzonitrile. The 2-(alkylthio)benzonitrile is subsequently reacted with a halogenation agent in the presence of water to give the 1,2-benzisothiazolin-3-one. With this method a recycling of intermediate products obtained during the preparation of the 1,2-benzisothiazolin-3-one is almost impossible. This makes the method very costly.

The object underlying the present invention is therefore to provide an improved method for producing a 1,2-benzisothiazolin-3-one. The method should not have the above mentioned disadvantages of the prior art or have them only to a significantly less extend. The method should be carried out more simply, saver and more cost efficient than those described in the state of the art.

This object is solved by a method for producing a 1,2-benzisothiazolin-3-one compound of the general formula (I)

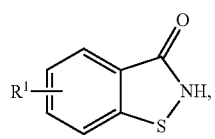

(I)

wherein $R^1$ is selected from the group consisting of hydrogen, unsubstituted or at least monosubstituted $C_1$-$C_{10}$-alkyl, $OR^2$, $C(O)OR^2$, F, Cl, Br, I and $NO_2$,
  wherein the substituents are selected from the group consisting of F, Cl, Br, I, OH, $NH_2$ and $C_5$-$C_{10}$-aryl,
  wherein
  $R^2$ is selected from the group consisting of hydrogen, unsubstituted or at least monosubstituted $C_1$-$C_{10}$-alkyl and unsubstituted or at least monosubstituted $C_5$-$C_{10}$-aryl,
  wherein the substituents are selected from the group consisting of F, Cl, Br, I, OH, $NH_2$, $C_1$-$C_{10}$-alkyl and $C_5$-$C_{10}$-aryl;

comprising the steps a) reacting a 2-halobenzonitrile compound of the general formula (II)

(II)

wherein
X is selected from the group consisting of F, Cl, Br and I;
with a thiol compound of the general formula (III)

(III), wherein
$R^3$ is selected from the group consisting of unsubstituted or at least monosubstituted $C_5$-$C_{30}$-alkyl, unsubstituted or at least monosubstituted $C_5$-$C_{30}$-aryl and unsubstituted or at least monosubstituted $C_6$-$C_{30}$-aralkyl,
  wherein the substituents are selected from the group consisting of F, Cl, Br, I, OH, $NH_2$, $C_1$-$C_{10}$-alkyl and $OR^4$,
  wherein
  $R^4$ is hydrogen or $C_1$-$C_{10}$-alkyl;
in the presence of at least one base (B) to form an intermediate of the general formula (IV)

(IV)

b) reacting the intermediate of the general formula (IV) obtained in step a) with a halogenation agent in the presence of water to form a reaction mixture (RM), comprising the 1,2-benzisothiazolin-3-one of the general formula (I) and a halide compound of the general formula (V)

(V), wherein
$X^1$ is Cl or Br.

It has surprisingly been found that the thiol compound (III), which has from 5 to 30 carbon atoms can be used for the preparation of a 1,2-benzisothiazolin-3-one starting from a 2-halobenzonitrile compound.

The use of a thiol compound having from 5 to 30 carbon atoms is advantageous as these thiols are semivolatile and have only a light odor. As these thiols are semivolatile, safety and environmental problems can be reduced compared to the methods described in the state of the art.

Moreover, the halide compound (V) obtained in step b) as well is semivolatile and furthermore it is non-soluble in water. This makes it possible, in one embodiment of the present invention, to separate the halide compound (V) from the 1,2-benzisothiazolin-3-one compound (I) and subsequently to react the halide compound (V) with a sulfide compound to give the thiol compound (III) having from 5 to 30 carbon atoms. This thiol compound (III) can be recycled to step a). This makes the method according to the present invention very economical and highly cost efficient.

Step a)

In step a) of the present invention a 2-halobenzonitrile compound (II) is reacted with a thiol compound (III) in the presence of at least one base (B) to form an intermediate (IV).

"A 2-halobenzonitrile compound (II)" within the context of the present invention means precisely one 2-halobenzonitrile compound (II) and also a mixture of two or more 2-halobenzonitrile compounds (II).

"A thiol compound (III)" within the context of the present invention means precisely one thiol compound (III) and also a mixture of two or more thiol compounds (III).

According to the present invention a 2-halobenzonitrile compound (II) is used.

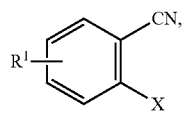
(II)

wherein $R^1$ is selected from the group consisting of hydrogen, unsubstituted or at least monosubstituted $OR^2$, $C(O)OR^2$, F, Cl, Br, I and $NO_2$, wherein the substituents are selected from the group consisting of F, Cl, Br, I, OH, $NH_2$ and $C_5$-$C_{10}$-aryl, wherein $R^2$ is selected from the group consisting of hydrogen, unsubstituted or at least monosubstituted $C_1$-$C_{10}$-alkyl and unsubstituted or at least monosubstituted $C_5$-$C_{10}$-aryl, wherein the substituents are selected from the group consisting of F, Cl, Br, I, OH, $NH_2$, $C_1$-$C_{10}$-alkyl and $C_5$-$C_{10}$-aryl;

X is selected from the group consisting of F, Cl, Br and I.

In a preferred embodiment of the present invention a 2-halobenzonitrile compound (II) is used, wherein the substituents have the following meanings:

$R^1$ is selected from the group consisting of hydrogen, $C_1$-$C_4$-alkyl, $OR^2$, $C(O)OR^2$, Cl, Br, I and $NO_2$, wherein $R^2$ is hydrogen or $C_1$-$C_4$-alkyl;

X is Cl or Br.

In a particularly preferred embodiment of the present invention a 2-halobenzonitrile compound (II) is used, wherein the substituents have the following meanings:

$R^1$ is selected from the group consisting of hydrogen, methyl, ethyl, tert-butyl, methoxy, carboxy, methoxy carbonyl, ethoxy carbonyl, propoxy carbonyl, Cl and $NO_2$;

X is Cl or Br.

Preferably the 2-halobenzonitrile compound (II) is selected from the group consisting of 2-chlorobenzonitrile, 2-bromobenzonitrile, 3-methyl-2-chlorobenzonitrile, 5-tert-butyl-2-chlorobenzonitrile, 4-methoxy-2-chlorobenzonitrile, 2-chloro-3-nitrobenzonitrile, 4-methoxycarbonyl-2-chlorobenzonitrile, 4-carboxy-2-chlorobenzonitrile and 2,4-dichlorobenzonitrile.

In a particularly preferred embodiment, the 2-halobenzonitrile compound (II) selected from the group consisting of 2-chlorobenzonitrile and 2-bromobenzonitrile.

Within the context of the present invention, definitions such as $C_1$-$C_{10}$-alkyl as for example defined above in formula (II) for $R^1$ mean that this substituent (radical) is an alkyl radical with a carbon atom number from 1 to 10.

Within the context of the present invention, definitions such as $C_1$-$C_4$-alkyl as for example defined above in formula (II) for $R^1$ mean that this substituent (radical) is an alkyl radical with a carbon atom number from 1 to 4.

Within the context of the present invention, definitions such as $C_5$-$C_{30}$-alkyl as for example defined below in formula (III) for $R^3$ mean that this substituent (radical) is an alkyl radical with a carbon atom number from 5 to 30.

The alkyl radical may be linear or branched and also optionally cyclic. Alkyl radicals which have both a cyclic component and also a linear component likewise fall under this definition.

Examples of $C_1$-$C_{10}$-alkyl are methyl, ethyl, n-propyl, sec-propyl, n-butyl, sec-butyl, isobutyl, 2-ethylhexyl, tert-butyl (tert-bu/t-Bu), pentyl, hexyl, heptyl, cyclohexyl, octyl, nonyl and decyl. Examples of $C_1$-$C_4$-alkyl are methyl, ethyl, n-propyl, sec-propyl, n-butyl, sec-butyl, isobutyl and tert-butyl (tert-bu/t-Bu). Examples of $C_5$-$C_{30}$-alkyl are pentyl, hexyl, heptyl, cyclohexyl, octyl, nonyl, decyl, undecyl, dodecyl and octadecyl.

Within the context of the present invention, the term "aryl", as for example defined above for the radical $R^2$ in formula (II) means that the substituent (radical) is an aromatic. The aromatic may be a monocyclic, bicyclic or optionally polycyclic aromatic. In the case of polycyclic aromatics, individual cycles can optionally be completely or partially saturated. Preferred examples of aryl are phenyl, naphthyl or anthracyl, in particular phenyl.

The 2-halobenzonitrile compound (II) can be prepared by any method known to the skilled person.

According to the present invention the 2-halobenzonitrile compound (II) is reacted with a thiol (III)

wherein $R^3$ is selected from the group consisting of unsubstituted or at least monosubstituted $C_5$-$C_{30}$-alkyl, unsubstituted or at least monosubstituted $C_5$-$C_{30}$-aryl and unsubstituted or at least monosubstituted $C_6$-$C_{30}$-aralkyl, wherein the substituents are selected from the group consisting of F, Cl, Br, I, OH, $NH_2$, $C_1$-$C_{10}$-alkyl and $OR^4$, wherein $R^4$ is hydrogen or $C_1$-$C_{10}$-alkyl.

In a preferred embodiment a thiol compound (III) is used, wherein the substituents have the following meanings:

$R^3$ is selected from the group consisting of unsubstituted or at least monosubstituted $C_5$-$C_{22}$-alkyl, unsubstituted or at least monosubstituted $C_5$-$C_{14}$-aryl and unsubstituted or at least monosubstituted $C_7$-$C_{18}$-aralkyl, wherein the substituents are selected from the group consisting of F, Cl, Br, I, OH, $NH_2$, $C_1$-$C_8$-alkyl and $OR^4$, wherein $R^4$ is hydrogen or $C_1$-$C_4$-alkyl.

In a particularly preferred embodiment a thiol compound (III) is used, wherein the substituents have the following meanings:

$R^3$ is unsubstituted or at least monosubstituted $C_5$-$C_{22}$-alkyl or unsubstituted or at least monosubstituted $C_7$-$C_{18}$-aralkyl,
   wherein the substituents are selected from the group consisting of F, Cl, Br, I, $C_1$-$C_8$-alkyl and $OR^4$,
   wherein
   $R^4$ is $C_1$-$C_4$-alkyl.

In a further particularly preferred embodiment a thiol compound (III) is used, wherein the substituents have the following meanings:
$R^3$ is unsubstituted or at least monosubstituted $C_5$-$C_{22}$-alkyl,
   wherein the substituents are selected from the group consisting of F, Cl, Br, I, $C_1$-$C_4$-alkyl and $OR^4$,
   wherein
   $R^4$ is $C_1$-$C_4$-alkyl.

Particular preference is given to a thiol compound of the general formula (III) selected from the group consisting of n-octadecanethiol, n-octanethiol, n-dodecanethiol, 2-tert-butyl-benzylmercaptan, 3-tert-butyl-benzylmercaptan and 4-tert-butyl-benzylmercaptan.

Within the context of the present invention, the term "aralkyl", as for example defined above for the radical $R^3$ in formula (III), means that the substituent is an alkyl radical that is in turn substituted with an aryl radical. In other words, the term "aralkyl" describes an alkylene that is substituted with an aryl radical. The aryl radical may be for example an aryl as per the above definitions.

Methods for the preparation of a thiol compound (III) are known to the skilled person.

According to the present invention step a), the reaction of the 2-halobenzonitrile compound (II) with the thiol compound (III), is carried out in the presence of at least one base (B).

Suitable at least one bases (B), that can be used in step a) of the present invention, are known to the skilled person.

"At least one base (B)" within the context of the present invention means precisely one base and also a mixture of two or more bases. Preferably the at least one base (B) comprises a base selected from the group consisting of metal hydroxides, metal carbonates and metal alkoholates. Particularly preferably the at least one base (B) comprises a base selected from the group consisting of alkali metal hydroxides, alkali metal carbonates and alkali metal alkoholates. More preferably the at least one base (B) comprises a base selected from the group consisting of sodium hydroxide, potassium hydroxide, sodium carbonate, potassium carbonate, sodium methylate and sodium ethylate. Most preferably the at least one base (B) comprises sodium hydroxide.

In a further preferred embodiment of the present invention, the at least one base (B) is sodium hydroxide. In a most preferred embodiment of the present invention, the at least one base (B2) is a solution of 20 to 50% by weight of sodium hydroxide in water, based on the total amount of sodium hydroxide and water.

During the reaction of the 2-halobenzonitrile compound (II) with the thiol compound (III) in the presence of the at least one base (B) an intermediate (IV) is formed

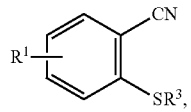

(IV)

wherein
$R^1$ is selected from the group consisting of hydrogen, unsubstituted or at least monosubstituted $C_1$-$C_{10}$-alkyl, $OR^2$, $C(O)OR^2$, F, Cl, Br, I and $NO_2$,
   wherein the substituents are selected from the group consisting of F, Cl, Br, I, OH, $NH_2$ and $C_5$-$C_{10}$-aryl,
   wherein
   $R^2$ is selected from the group consisting of hydrogen, unsubstituted or at least monosubstituted $C_1$-$C_{10}$-alkyl and unsubstituted or at least monosubstituted $C_5$-$C_{10}$-aryl,
   wherein the substituents are selected from the group consisting of F, Cl, Br, I, OH, $NH_2$, $C_1$-$C_{10}$-alkyl and $C_5$-$C_{10}$-aryl;
$R^3$ is selected from the group consisting of unsubstituted or at least monosubstituted $C_5$-$C_{30}$-alkyl, unsubstituted or at least monosubstituted $C_5$-$C_{30}$-aryl and unsubstituted or at least monosubstituted $C_6$-$C_{30}$-aralkyl,
   wherein the substituents are selected from the group consisting of F, Cl, Br, I, OH, $NH_2$, $C_1$-$C_{10}$-alkyl and $OR^4$,
   wherein
   $R^4$ is hydrogen or $C_1$-$C_{10}$-alkyl.

In a preferred embodiment of the present invention an intermediate (IV) is formed, where the substituents have the following meanings:
$R^1$ is selected from the group consisting of hydrogen, $C_1$-$C_4$-alkyl, $OR^2$, $C(O)OR^2$, Cl, Br, I and $NO_2$,
   wherein
   $R^2$ is hydrogen or $C_1$-$C_4$-alkyl;
$R^3$ is selected from the group consisting of unsubstituted or at least monosubstituted $C_5$-$C_{22}$-alkyl, unsubstituted or at least monosubstituted $C_5$-$C_{14}$-aryl and unsubstituted or at least monosubstituted $C_7$-$C_{18}$-aralkyl,
   wherein the substituents are selected from the group consisting of F, Cl, Br, I, OH, $NH_2$, $C_1$-$C_8$-alkyl and $OR^4$,
   wherein
   $R^4$ is hydrogen or $C_1$-$C_4$-alkyl.

In a particularly preferred embodiment of the present invention an intermediate (IV) is formed, where the substituents have the following meanings:
$R^1$ is selected from the group consisting of hydrogen, methyl, ethyl, tert-butyl, methoxy, carboxy, methoxy carbonyl, ethoxy carbonyl, propoxy carbonyl, Cl and $NO_2$;
$R^3$ is unsubstituted or at least monosubstituted $C_5$-$C_{22}$-alkyl or unsubstituted or at least monosubstituted $C_7$-$C_{18}$-aralkyl,
   wherein the substituents are selected from the group consisting of F, Cl, Br, I, $C_1$-$C_8$-alkyl and $OR^4$,
   wherein
   $R^4$ is $C_1$-$C_4$-alkyl.

It is known to the skilled person that $R^1$ and $R^2$ in formula (IV) is the same $R^1$ and $R^2$ as stated above for formula (II). Consequently, $R^1$ and $R^2$ in formula (IV) and in formula (II) have the same meanings and preferences.

Furthermore, it is known to the skilled person that $R^3$ and $R^4$ in formula (IV) is the same $R^3$ and $R^4$ as stated above for formula (III). Consequently, $R^3$ and $R^4$ in formula (IV) and in formula (III) have the same meanings and preferences.

In step a) the molar ratio of the 2-halobenzonitrile compound (II) to the thiol compound (III) is usually in the range of from 1:0.8 to 1:3, preferably of from 1:1 to 1:3 and particularly preferably of from 1:1 to 1:1.2.

The molar ratio of the 2-halobenzonitrile compound (II) to the at least one base (B) is generally in the range of from 1:0.8 to 1:3.5 preferably of from 1:0.8 to 1:1.5 and particularly preferably of from 1:1.03 to 1:1.2.

In one embodiment of the present invention step a) is carried out under an inertgas atmosphere. Suitable inert gases are known to the skilled person. Preferred inert gases are for example nitrogen or argon.

In one embodiment of the present invention step a) is carried out in the presence of a heterogeneous solvent system. A heterogeneous solvent system within the present invention means that at least one aqueous solvent and at least one organic solvent, are used, which are immiscible in each other. Consequently a heterogeneous solvent system means that two liquid phases are present.

Another object of the present invention is therefore a method, wherein step a) is carried out in the presence of a heterogeneous solvent system, comprising an aqueous solvent and an organic solvent.

"An organic solvent" within the present invention means precisely one organic solvent and also mixtures of two or more organic solvents.

"An aqueous solvent" within the present invention means a solvent that comprises water and optionally at least one further solvent that is miscible with water. In a preferred embodiment the aqueous solvent comprises at least 70% by weight, in particular at least 80% by weight and more preferably at least 90% by weight of water based on the total amount of the aqueous solvent. In a particularly preferred embodiment the aqueous solvent consists of water.

Suitable organic solvents that can be comprised in the heterogeneous solvent system are known to the skilled person. Preferably, the organic solvent comprised in the heterogeneous solvent system is at least one organic solvent selected from the group consisting of benzene, toluene, xylenes, aryl halides and $C_5$-$C_{14}$-alkanes.

Another object of the present invention is therefore a method, wherein the organic solvent comprised in the heterogeneous solvent system in step a) is selected from the group consisting of benzene, toluene, xylenes, aryl halides and $C_5$-$C_{14}$-alkanes.

Xylenes comprise 1,2-dimethylbenzene, 1,3-dimethylbenzene and 1,4-dimethylbenzene.

Suitable aryl halides are known to the skilled person. Preferred aryl halides within the present invention are selected from the group consisting of chlorobenzene, 1,2-dichlorobenzene, 1,3-dichlorobenzene, 1,4-dichlorobenzene and mixtures thereof.

$C_5$-$C_{14}$-alkanes are alkanes having a carbon atom number of from 5 to 14. The alkanes can be linear or branched and also optionally cyclic. Alkanes which have both a cyclic component and also a linear component likewise fall under this definition. Preferred $C_5$-$C_{14}$-alkanes are selected from the group consisting of n-hexane, n-heptane, cyclohexane and methylcyclohexane.

In a further preferred embodiment the organic solvent comprised in the heterogeneous solvent system in which step a) is carried out comprises at least one organic solvent selected from the group consisting of benzene, toluene, xylenes, n-hexane, n-heptane, cyclohexane, methyl cyclohexane, chlorobenzene, 1,2-dichlorobenzene, 1,3-dichlorobenzene and 1,4-dichlorobenzene.

In a particularly preferred embodiment, the organic solvent comprises chlorobenzene. Preferably the organic solvent comprises at least 70% by weight, in particular at least 80% by weight and more preferably at least 90% by weight of chlorobenzene based on the total amount of the organic solvent. Most preferably, the organic solvent consists of chlorobenzene.

The weight ratio of the aqueous solvent to the organic solvent is usually in the range of from 1:0.5 to 1:10, if a heterogeneous solvent system is used in step a).

The molar ratio of the 2-halobenzonitril compound (II) to the organic solvent is preferably in the range of from 1:0 to 1:4 and particularly preferably of from 1:0 to 1:1.

In one embodiment of the present invention step a) is carried out in the presence of a heterogeneous solvent system and furthermore at least one phase transfer catalyst is used.

Preferably the at least one phase transfer catalyst is selected from the group consisting of quaternary ammonium salts, quaternary phosphonium salts and crown ethers.

Another object of the present invention is therefore a method, wherein step a) is carried out in the presence of at least one phase transfer catalyst selected from the group consisting of quaternary ammonium salts, quaternary phosphonium salts and crown ethers.

Suitable quaternary ammonium salts are known to the skilled person. For example, the quaternary ammonia salt can be selected from the group consisting of benzyltriethylammonium bromide, benzyltriethylammonium chloride, benzyltrimethylammonium bromide, benzyltrimethylammonium chloride, hexadecyltriethylammonium bromide, hexadecyltriethylammonium chloride, hexadecyltrimethylammonium bromide, hexadecyltrimethylammonium chloride, dodecyltrimethylammonium bromide, dodecyltrimethylammonium chloride, octyltriethylammonium bromide, octyltriethylammonium chloride, tetra-butylammonium bromide, tetra-butylammonium chloride, tetraethylammonium bromide, tetraethylammonium chloride, trioctylmethylammonium bromide, trioctylmethylammonium chloride, triethylphenylammonium bromide and triethylphenylammonium chloride.

Preferably the quaternary ammonium salt is selected from the group consisting of hexadecyltrimethylammonium bromide, hexadecyltrimethylammonium chloride, dodecyltrimethylammonium bromide, dodecyltrimethylammonium chloride, octyltriethylammonium bromide, tetra-butylammonium bromide, tetra-butylammonium chloride, triethylphenylammonium bromide and triethylphenylammonium chloride.

Suitable quaternary phosphonium salts are known to the skilled person. Preferably the quaternary phosphonium salt is selected from the group consisting of hexadecyltriethylphosphonium bromide, hexadecyltriethylphosphonium chloride, hexadecyltributylphosphonium bromide, hexadecyltributylphosphonium chloride, tetra-butylphosphonium bromide, tetra-butylphosphonium chloride, trioctylethylphosphonium bromide, trioctylethylphosphonium chloride, tetraphenylphosphonium bromide, tetraphenylphosphonium chloride, hexadecyltrimethylphosphonium chloride and hexadecyltrimethylphosphonium bromide.

Particularly preferably the quaternary phosphonium salt is selected from the group consisting of tetra-butylphosphonium bromide, tetra-butylphosphonium chloride and hexadecyltrimethylphosphonium chloride.

Suitable crown ethers are known to the skilled person. Preferably the crown ether is selected from the group consisting of 18-crown-6, dibenzo-18-crown-6, benzo-18-crown-6 and dicyclohexyl-18-crown-6.

Particularly preferably the crown ether is selected from the group consisting of 18-crown-6, dibenzo-18-crown-6 and dicyclohexyl-18-crown-6.

Therefore, in a particularly preferred embodiment step a) is carried out in the presence of at least one phase transfer catalyst selected from the group consisting of hexadecyltrimethylammonium bromide, hexadecyltrimethylammonium chloride, dodecyltrimethylammonium bromide, dodecyltrimethylammonium chloride, octyltriethylammonium bromide, tetra-butylammonium bromide, tetra-butylammonium chloride, triethylphenylammonium bromide, triethylphenylammonium chloride, tetrabutylphosphonium bromide, tetrabutylphosphonium chloride, hexadecyltrimethylphosphonium chloride, 18-crown-6, dibenzo-18-crown-6 and dicyclohexyl-18-crown-6.

In a most preferred embodiment step a) is carried out in the presence of at least one phase transfer catalyst selected from the group consisting of tetra-butylammonium bromide and tetra-butylammonium chloride.

The weight ratio of the phase transfer catalyst to the 2-halobenzonitrile compound (II) is normally in the range of from 0.02:1 to 0.4:1, preferably of from 0.05:1 to 0.15:1.

If a heterogeneous solvent system is used in step a), the temperature during step a) depends on the heterogeneous solvent system. Usually, the temperature in step a) is below the boiling temperature of the heterogeneous solvent system at the pressure at which step a) is carried out and above the melting temperature of the heterogeneous solvent system at the pressure at which step a) is carried out.

In one embodiment of the present invention step a) is carried out in the presence of a heterogeneous solvent system and the reaction temperature is in the range of from 20 to 120° C., preferably of from 30 to 100° C. and more preferably of from 50 to 75° C.

Step a) can be carried out at any pressure. It can be carried out at positive pressure as well as at negative pressure. In a preferred embodiment, step a) is carried out in the presence of a heterogeneous solvent system and at a pressure of from 0.1 to 100000 bar, particularly preferably from 100 to 10000 bar.

In another preferred embodiment of the present invention step a) is carried out in the presence of a heterogeneous solvent system and the reaction time is in the range of from 0.5 to 40 hours, preferably of from 0.5 to 25 hours and particularly preferably of from 2 to 12 hours.

In another preferred embodiment of the present invention step a) is carried out in the presence of a homogeneous solvent system. A homogeneous solvent system means that at least one solvent is used. If two or more solvents are used then the two or more solvents are fully miscible. Consequently, a homogeneous solvent system means that only one liquid phase is present.

In one embodiment step a) is carried out in the presence of a homogeneous solvent system comprising at least one polar aprotic solvent.

Another object of the present invention is therefore a method, wherein step a) is carried out in the presence of a homogeneous solvent system, comprising at least one polar aprotic solvent.

Preferably, the at least one polar aprotic solvent is selected from the group consisting of N-methyl pyrrolidone, dimethyl sulfoxide, N,N-dimethylformamide, N,N-diethylformamide and N-ethyl pyrrolidone.

If a homogeneous solvent system is used in step a), the temperature during step a) depends on the homogeneous solvent system. Usually, the temperature in step a) is below the boiling temperature of the homogeneous solvent system at the pressure at which step a) is carried out and above the melting temperature of the homogeneous solvent system at the pressure at which step a) is carried out.

In a further preferred embodiment step a) is carried out in the presence of a homogeneous solvent system and the reaction temperature is in the range of from 0 to 200° C., preferably of from 30 to 150° C.

In another preferred embodiment, step a) is carried out in the presence of a homogeneous solvent system and at a pressure of from 0.1 to 100000 bar, particularly preferably from 100 to 10000 bar.

In another preferred embodiment step a) is carried out in the presence of a homogeneous solvent system and the reaction time is in the range of from 1 to 10 hours.

In step a) the intermediate (IV) is formed.

In one embodiment of the present invention the intermediate (IV) is isolated after step a) and before step b).

Methods to isolate the intermediate (IV) are known to the skilled person. For example, the intermediate (IV) can be isolated by crystallization or by phase separation.

Preferably, the intermediate (IV) is isolated by phase separation.

In a further embodiment of the present invention step b) directly follows step a) without isolating the intermediate (IV).

It is known to the skilled person that in step a) during the reaction of the 2-halobenzonitrile compound (II) with the thiol compound (III) not only the intermediate (IV) is formed, but also by-products are formed. Typical by-products formed in step a) are for example hydrogen halides.

Step b)

In step b) the intermediate (IV) obtained in step a) is reacted with a halogenation agent in the presence of water to form a reaction mixture (RM).

Within the present invention "a halogenation agent" means precisely one halogenation agent but also a mixture of two or more halogenation agents.

Suitable halogenation agents are known to the skilled person. Preferably, the halogenation agent is selected from the group consisting of chlorine, bromine, sulfuryl chloride and sulfuryl bromide.

Another object of the present invention is therefore a method, wherein in step b) the halogenation agent is selected from the group consisting of chlorine, bromine, sulfuryl chloride and sulfuryl bromide.

Sulfuryl chloride and chlorine are particularly preferred as halogenation agent.

In one embodiment of the present invention the chlorine used as a halogenation agent is generated in-situ by oxidizing a chloride. The bromine as well can be generated in-situ by oxidizing a bromide. Methods to oxidize a chloride and/or a bromide are known to the skilled person.

In one embodiment of the present invention the halogenation agent and the water are added gradually and simultaneously to the intermediate (IV).

In another embodiment the water is already present when the halogenation agent is added to the intermediate (IV).

The molar ratio of the halogenation agent to the intermediate (IV) is usually in a range of from 0.8:1 to 3:1, preferably of from 1:1 to 1.5:1.

The molar ratio of the water to the intermediate (IV) is usually in the range of from 1:1 to 5:1, preferably of from 1:1 to 3:1.

Step b) is usually carried out in the presence of a solvent. Suitable solvents are known to the skilled person. Preferably the solvent is inert to the reaction carried out in step b).

In a preferred embodiment step b) is carried out in the presence of an organic solvent. Suitable organic solvents in which step b) can be carried out are known to the skilled person. Preferably, the organic solvent in which step b) is carried out is at least one organic solvent selected from the group consisting of benzene, toluene, xylenes, aryl halides, $C_5$-$C_{14}$-alkanes and alkyl halides.

Another object of the present invention is therefore a method wherein step b) is carried out in the presence of an organic solvent and the organic solvent is selected from the group consisting of benzene, toluene, xylenes, aryl halides, $C_5$-$C_{14}$-alkanes, and alkyl halides.

Xylenes comprise 1,2-dimethylbenzene, 1,3-dimethylbenzene and 1,4-dimethylbenzene.

Suitable aryl halides are known to the skilled person. Preferred aryl halides within the present invention are selected from the group consisting of chlorobenzene, 1,2-dichlorobenzene, 1,3-dichlorobenzene, 1,4-dichlorobenzene and mixtures thereof.

Suitable alkyl halides are as well known to the skilled person. Within the present invention preferred alkyl halides are selected from the group consisting of chloroform (IUPAC-name: Trichlormethane) and 1,2-dichlorethane.

$C_5$-$C_{14}$-alkanes are alkanes having a carbon atom number of from 5 to 14. The alkanes can be linear or branched and also optionally cyclic. Alkanes which have both a cyclic component and also a linear component likewise fall under this definition. Preferred $C_5$-$C_{14}$-alkanes are selected from the group consisting of n-hexane, n-heptane, cyclohexane and methylcyclohexane.

In a further preferred embodiment the organic solvent in which step b) is carried out comprises at least one organic solvent selected from the group consisting of benzene, toluene, xylenes, n-hexane, n-heptane, cyclohexane, methyl cyclohexane, chlorobenzene, 1,2-dichlorobenzene, 1,3-dichlorobenzene, 1,4-dichlorobenzene, chloroform (IUPAC-name: Trichlormethane) and 1,2-dichlorethane.

If an organic solvent is used in step b), the reaction temperature in step b) depends on the organic solvent. Usually the reaction temperature in step b) is below the boiling temperature of the organic solvent at the pressure at which step b) is carried out and above the melting temperature of the organic solvent at the pressure at which step b) is carried out.

Step b) is preferably carried out at a temperature in the range of from 0 to 50° C., particularly preferably of from 10 to 40° C.

The reaction time in step b) is preferably in the range of from 1 to 20 hours and particularly preferably in the range of from 4 to 12 hours.

In step b) the reaction mixture (RM) is formed, which comprises the 1,2-benzisothiazolin-3-one compound (I) and the halide compound (V).

The reaction mixture (RM) comprises the 1,2-benzisothiazolin-3-one compound (I)

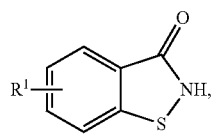

(I)

wherein
R$^1$ is selected from the group consisting of hydrogen, unsubstituted or at least monosubstituted $C_1$-$C_{10}$-alkyl, OR$^2$, C(O)OR$^2$, F, Cl, Br, I and NO$_2$,
wherein the substituents are selected from the group consisting of F, Cl, Br, I, OH, NH$_2$ and $C_5$-$C_{10}$-aryl,
wherein
R$^2$ is selected from the group consisting of hydrogen, unsubstituted or at least monosubstituted $C_1$-$C_{10}$-alkyl and unsubstituted or at least monosubstituted $C_5$-$C_{10}$-aryl, wherein the substituents are selected from the group consisting of F, Cl, Br, I, OH, NH$_2$, $C_1$-$C_{10}$-alkyl and $C_5$-$C_{10}$-aryl.

In a preferred embodiment of the present invention the reaction mixture (RM) obtained in step b) comprises the 1,2-benzisothiazolin-3-one compound (I), wherein the substituents have the following meanings:
R$^1$ is selected from the group consisting of hydrogen, $C_1$-$C_4$-alkyl, OR$^2$, C(O)OR$^2$, Cl, Br, I and NO$_2$,
wherein
R$^2$ is hydrogen or $C_1$-$C_4$-alkyl.

In a particularly preferred embodiment of the present invention the reaction mixture (RM) obtained in step b) comprises the 1,2-benzisothiazolin-3-one compound (I), wherein the substituents have the following meanings:
R$^1$ is selected from the group consisting of hydrogen, methyl, ethyl, tert-butyl, methoxy, carboxy, methoxy carbonyl, ethoxy carbonyl, propoxy carbonyl, Cl and NO$_2$.

Preferably the reaction mixture (RM) obtained in step b) comprises the 1,2-benzisothiazolin-3-one compound (I) selected from the group consisting of 1,2-benzisothiazolin-3-one (BIT), 3-methyl-1,2-benzisothiazolin-3-one, 5-tert-butyl-1,2-benzisothiazolin-3-one, 4-methoxy-1,2-benzisothiazolin-3-one, 3-nitro1,2-benzisothiazolin-3-one, 4-methoxycarbonyl-1,2-benzisothiazolin-3-one, 4-carboxy-1,2-benzisothiazolin-3-one and 4-chloro-1,2-benzisothiazolin-3-one.

In an especially preferred embodiment, the reaction mixture (RM) obtained in step b) comprises the 1,2-benzisothiazolin-3-one compound (I) and the 1,2-benzisothiazolin-3-one compound (I) comprises 1,2-benzisothiazolin-3-one (BIT).

It is known to the skilled person, that R$^1$ and R$^2$ in formula (I) is the same R$^1$ and R$^2$ as stated above for formula (II) and also for formula (IV). Consequently, R$^1$ and R$^2$ in formula (I), in formula (II) and in formula (IV) have the same meanings and preferences.

Furthermore, the reaction mixture (RM) comprises the halide compound (V)

wherein
R$^3$ is selected from the group consisting of unsubstituted or at least monosubstituted $C_5$-$C_{30}$-alkyl, unsubstituted or at least monosubstituted $C_5$-$C_{30}$-aryl and unsubstituted or at least monosubstituted $C_6$-$C_{30}$-aralkyl,
wherein the substituents are selected from the group consisting of F, Cl, Br, I, OH, NH$_2$, $C_1$-$C_{10}$-alkyl and OR$^4$,
wherein
R$^4$ is hydrogen or $C_1$-$C_{10}$-alkyl;
X$^1$ is Cl or Br.

In a preferred embodiment the reaction mixture (RM) comprises the halide compound (V), wherein the substituents have the following meanings:
R$^3$ is selected from the group consisting of unsubstituted or at least monosubstituted $C_5$-$C_{22}$-alkyl, unsubstituted or at least monosubstituted $C_5$-$C_{14}$-aryl and unsubstituted or at least monosubstituted $C_7$-$C_{18}$-aralkyl,
wherein the substituents are selected from the group consisting of F, Cl, Br, I, OH, NH$_2$, $C_1$-$C_8$-alkyl and OR$^4$,
wherein
R$^4$ is hydrogen or $C_1$-$C_4$-alkyl;
X$^1$ is Cl or Br.

In a particularly preferred embodiment the reaction mixture (RM) comprises the halide compound (V), wherein the substituents have the following meanings:

$R^3$ is unsubstituted or at least monosubstituted $C_5$-$C_{22}$-alkyl or unsubstituted or at least monosubstituted $C_7$-$C_{18}$-aralkyl, wherein the substituents are selected from the group consisting of F, Cl, Br, I, $C_1$-$C_8$-alkyl and $OR^4$,
wherein
$R^4$ is $C_1$-$C_4$-alkyl;
$X^1$ is Cl or Br.

In a further particularly preferred embodiment the reaction mixture (RM) comprises the halide compound (V), wherein the substituents have the following meanings:

$R^3$ is unsubstituted or at least monosubstituted $C_5$-$C_{22}$-alkyl, wherein the substituents are selected from the group consisting of F, Cl, Br, I, $C_1$-$C_4$-alkyl and $OR^4$,
wherein
$R^4$ is $C_1$-$C_4$-alkyl;
$X^1$ is Cl or Br.

Particularly preferably the reaction mixture (RM) comprises a halide compound (V) selected from the group consisting of n-octadecylchlorid, n-octadecylbromid, n-octylchlorid, n-octylbromid, dodecylchloride, docecylbromide, 2-tert-butyl-benzylchloride, 2-tert-butyl-benzylbromide, 3-tert-butyl-benzylchloride, 3-tert-butyl-benzylbromide, 4-tert-butyl-benzylchloride and 4-tert-butyl-benzylbromide.

It is known to the skilled person that the meaning of the substituent $X^1$ in formula (V) depends on the halogenation agent used in step b). If chlorine or sulfuryl chloride is used as halogenation agent, then $X^1$ is Cl. If bromine or sulfuryl bromide is used as halogenation agent, then $X^1$ is Br.

Furthermore, it is known to the skilled person that $R^3$ and $R^4$ in formula (V) is the same $R^3$ and $R^4$ as stated above for formula (III) and formula (IV). Consequently, $R^3$ and $R^4$ in formula (V), in formula (III) and in formula (IV) have the same meanings and preferences.

After step b) the 1,2-benzisothiazolin-3-one compound (I) is usually separated from the reaction mixture (RM) formed in step b). Methods to separate the 1,2-benzisothiazolin-3-one compound (I) from the reaction mixture (RM) are known to the skilled person.

In one embodiment of the present invention step b) is followed by the following steps:

c) adding water and a second base (B2) to the reaction mixture (RM) obtained in step b) to give a first phase, comprising the 1,2-benzisothiazolin-3-one compound (I) and a second phase comprising the halide compound (V), d) separating the first phase from the second phase.

Another object of the present invention is therefore a method wherein step b) is followed by the following steps:

c) adding water and a second base (B2) to the reaction mixture (RM) obtained in step b) to give a first phase, comprising the 1,2-benzisothioazolin-3-one compound (I) and a second phase, comprising the halide compound (V), d) separating the first phase from the second phase.

"A second base (B2)" within the context of the present invention means precisely one second base and also a mixture of two or more second bases.

Preferably the second base (B2) comprises a base selected from the group consisting of metal hydroxides, metal carbonates and metal alkoholates. Particularly preferably the second base (B2) comprises a base selected from the group consisting of alkali metal hydroxides, alkali metal carbonates and alkali metal alkoholates. More preferably the second base (B2) comprises a base selected from the group consisting of sodium hydroxide, potassium hydroxide, sodium carbonate, potassium carbonate, sodium methylate and sodium ethylate. Most preferably the second base (B2) comprises sodium hydroxide. In a further preferred embodiment of the present invention, the second base (B2) is sodium hydroxide. In a most preferred embodiment of the present invention, the second base (B2) is a solution of 20 to 50% by weight of sodium hydroxide in water, based on the total amount of sodium hydroxide and water.

An object of the present invention is therefore a method wherein the second base (B2) is selected from the group consisting of metal hydroxides, metal carbonates and metal alkoholates.

Another object of the present invention is therefore a method wherein the base (B) and optionally the second base (B2) are independent of each other selected from the group consisting of metal hydroxides, metal carbonates and metal alkoholates.

The molar ratio of the 1,2-benzisothiazolin-3-one compound (I) to the second base (B2) added in step c) is in one embodiment of the present invention in the range of from 1:1 to 1:3.

The second base (B2) in step c) is preferably added in an amount so that the pH-value of the first phase obtained in step c) is in the range of from 8 to 11, preferably of from 9 to 10.

The molar ratio of the 1,2-benzisothiazolin-3-one compound (I) to the water added in step c) is in one embodiment of the present invention in the range of from 1:1 to 1:8, preferably from 1:2 to 1:4.

The person skilled in the art knows, that when adding water and the second base (B2) in step c) to the reaction mixture (RM) at least part of the 1,2-benzisothiazolin-3-one compound (I) is deprotonated to give a 1,2-benzisothiazolin-3-one compound metal salt. This 1,2-benzisothiazolin-3-one compound metal salt is soluble in water.

In step c) two phases are obtained. The first phase is an aqueous phase, comprising the 1,2-benzisothiazolin-3-one compound metal salt and water. The second phase is an organic phase, comprising the halide compound (V).

If an organic solvent is used in step b) this organic solvent is as well comprised in the second phase obtained in step c).

In one embodiment of the present invention step c) is carried out at a temperature in the range of from 40 to 100° C. preferably of from 60 to 80° C. and a reaction time in the range of from 0.5 to 4 hours, preferably of from 0.5 to 2 hours.

In a further embodiment of the present invention step c) is carried out at a temperature in the range of from 0 to 40° C., preferably of from 10 to 30° C. and a reaction time of from 1 to 4 hours, preferably of from 1 to 2 hours.

In step d) the first phase is separated from the second phase. Methods for the separation of the first phase from the second phase are known to the skilled person. The separation for example, can take place in a phase separation vessel.

In one embodiment of the present invention, after the separation in step d) an acid is added to the first phase. Suitable acids are known to the skilled person. For example, the acid can be selected from the group consisting of hydrochloric acid, sulfuric acid, nitric acid, acetic acid, oxalic acid, citric acid, methanesulfonic acid and mixtures thereof. Particularly preferred, the acid is an aqueous solution of 30% by weight of hydrochloric acid.

The pH-value of the first phase during the addition of the acid preferably drops to a value in the range of from 1 to 6, particularly preferably from 3 to 4.

When adding acid to the aqueous phase the 1,2-benzisothiazolin-3-one compound metal salt is neutralized and the 1,2-benzisothiazolin-3-one compound (I) precipitates and forms crystals. The thus obtained crystals of the 1,2-benzisothiazolin-3-one compound (I) can be separated from the water and optionally further solvents comprised in the first phase by any method known to the skilled person, for example, by filtration.

In a preferred embodiment step d) is followed by step e) in which the halide compound (V) comprised in the second phase is reacted with a sulfide compound to give a thiol compound (III).

Another object of the present invention is therefore a method, wherein step d) is followed by step e), in which the halide compound (V) comprised in the second phase is reacted with a sulfide compound to give a thiol compound (III).

Suitable sulfide compounds are known to the skilled person. Preferably the sulfide compound in step e) is selected from the group consisting of thiourea, metal bisulfide and metal sufide. More preferably, the sulfide compound in step e) is selected from the group consisting of thiourea, alkaline metal bisulfide and alkaline metal sulfide. Particularly preferably the sulfide compound in step e) is selected from the group consisting of thiourea, sodium bisulfide and sodium sulfide. In a further preferred embodiment, the sulfide compound is solution of 20 to 70% by weight of sodium bisulfide in water, based on the total weight of the sodium bisulfide and the water.

Another object of the present invention is therefore the method wherein the sulfide compound in step e) is selected from the group consisting of thiourea, a metal bisulfide and a metal sulfide.

The molar ratio of the halide compound of the general formula (V) to the sulfide compound is preferably in the range of from 1:1 to 1:3, particularly from 1:1.1 to 1:2.

Step e) is preferably carried out in the presence of a heterogeneous solvent system. Concerning the heterogeneous solvent system the same embodiments and preferences as described above for the heterogeneous solvent system in which step a) can be carried out hold true. Preferably, in step e) a phase transfer catalyst is used. Concerning the phase transfer catalyst the embodiments and preferences described above for the phase transfer catalyst used in step a) hold true as well.

Another object of the present invention is therefore the method wherein step c) is carried out in the presence of a heterogeneous solvent system, comprising an aqueous solvent and an organic solvent.

Step e) is preferably carried out at a temperature in the range of from 30 to 90° C. preferably of from 45 to 75° C.

The reaction time in step e) usually is in the range of from 2 to 25 hours preferably of from 5 to 15 hours.

In a particular preferred embodiment the thiol compound (III) obtained in step e) is recycled to step a).

Another object of the present invention is therefore a method wherein the thiol compound (III) obtained in step e) is recycled to step a).

In one embodiment of the present invention the thiol compound (III) obtained in step e) is recycled to step a) without any further separation and the heterogeneous solvent system used in step e) is as well recycled to step a) and can be used therein.

The recycling of at least the thiol compound (III) obtained in step e) to step a) makes the present invention highly cost efficient and time saving.

Furthermore, the thiol compound (III) has a high molecular weight and therefore a low volatility and a light odor. This reduces the safety and environmental problems in comparison to the methods described in the state of the art.

EXAMPLES

For the HPLC-measurements (high performance liquid chromatography) a FU LI 2000 HPLC-system with a Kromasil® C18 HPLC-Column having a pore size of 100 Å and a particle size of 7 μm was used. The length of the column was 250 mm, the inside diameter 4.6 mm. As mobile phase a 1:1-mixture of deionized water and methanol was used. 100 mg of the 1,2-benzisothiazolin-3-one (I) were dissolved in the mobile phase to give a total of 25 ml of the sample. The flow rate was 0.8 ml/min at a temperature of 25° C. The injection volume was 20 μl, the run time 20 min.

Example 1

Under nitrogen atmosphere, 100 g of chlorobenzene, 100 g of 2-chlorobenzonitrile (II), 219 g of n-octanethiol (III) and 4 g of tetra-butylammonium bromide are added into a 1000 ml four-necked flask with a stirrer, a thermometer, a dropping funnel and a condenser. At a temperature in the range of from 65 to 70° C. according to step a), 98.7 g of a 32% by weight sodium hydroxide solution in water are added dropwise. After the completion of the dropwise addition, the mixture is further reacted for 4 hours. The mixture is separated into an aqueous layer and an organic layer. The organic layer comprises 2-(octadecylthio)benzonitrile (IV) (381 g).

According to step b) 381 g of the organic layer, comprising 2-(octadecylthio)benzonitrile (IV) obtained in step a), 100 g of chlorobenzene and 32 g of water are added into a 1000 ml four-necked flask with a stirrer, a thermometer and a condenser. At a temperature in the range of from 20 to 30° C., 53 g chlorine are blown into the mixture over a period of 2 hours. The mixture is further heated to a temperature in the range of from 60 to 65° C. and then allowed to further react for 1 h. During the reaction the reaction mixture (RM) is formed. After completion of the reaction the reaction mixture (RM) is cooled to a temperature in the range of from 20 to 30° C. and according to step c) 200 g of water are added to the reaction mixture (RM). A 32% by weight sodium hydroxide solution is added dropwise to the reaction mixture (RM) to give a pH-value in the range of from 9 to 10. The mixture is heated to a temperature in the range of from 60 to 65° C. and according to step d) separated into a first phase and a second phase. The first phase is cooled to a temperature in the range of from 20 to 30° C. A 31% by weight hydrochloric acid solution is added dropwise to the first phase to give a pH-value in the range of from 3 to 4. Crystals of 1,2-benzisothiazolin-3-one precipitate. The precipitated crystals are collected by filtration, washed with water, and dried to obtain 1,2-benzisothiazolin-3-one (I) (102 g, HPLC>99%), the yield to 2-chlorobenzonitrile (II) is 93.5%.

The second phase (420 g) is distilled to obtain 1-chlorooctadecane (V) (210 g). 210 g of the 1-chlorooctadecane (V), 200 g of chlorobenzene, 180 g of a 32% by weight sodium bisulfide solution in water and 6 g of tetra-butylammonium bromide are added into a 1000 ml four-necked flask with a stirrer, a thermometer and a condenser. At a temperature in the range of from 65 to 70° C., the mixture is reacted for 16 h. The mixture is separated into an aqueous layer and an organic layer. The organic layer is n-octadecanethiol (III) (405 g).

Example 2

Under nitrogen atmosphere, 100 g of chlorobenzene, 100 g of 2-chlorobenzonitrile (II), 112 g of n-octanethiol (III) and 4 g of tetra-butylammonium bromide are added into a 500 ml four-necked flask with a stirrer, a thermometer, a dropping funnel and a condenser. At a temperature in the range of from 65 to 70° C. according to step a), 98 g of a 32% by weight sodium hydroxide solution in water are added dropwise. After the completion of the dropwise addition, the mixture is further reacted for 4 hours. The mixture is separated into an aqueous layer and an organic layer. The organic layer comprises 2-(octylthio)benzonitrile (IV) (279 g).

According to step b) 279 g of the organic layer, comprising the 2-(octylthio)benzonitrile (IV) obtained in step a), 200 g of chlorobenzene and 32 g of water are added into a 1000 ml four-necked flask with a stirrer, a thermometer and a condenser. At a temperature in the range of from 20 to 30° C., 54 g chlorine are blown into the mixture over a period of 2 hours. The mixture is further heated to a temperature in the range of from 60 to 65° C. and then allowed to further react for 1 h. During the reaction the reaction mixture (RM) is formed. After completion of the reaction the reaction mixture (RM) is cooled to a temperature in the range of from 20 to 30° C. and according to step c) 200 g of water are added to the reaction mixture (RM). A 32% by weight sodium hydroxide solution is added dropwise to the reaction mixture (RM) to give a pH-value in the range of from 9 to 10. The mixture is heated to a temperature in the range of from 60 to 65° C. and according to step d) separated into a first phase and a second phase. The first phase is cooled to a temperature in the range of from 20 to 30° C. A 31% by weight hydrochloric acid solution is added dropwise to the first phase to give a pH-value in the range of from 3 to 4. Crystals of 1,2-benzisothiazolin-3-one (I) precipitate. The precipitated crystals are collected by filtration, washed with water, and dried to obtain 1,2-benzisothiazolin-3-one (I) (103 g, HPLC>99%), the yield to 2-chlorobenzonitrile (II) is 94.5%.

The second phase (310 g) is distilled to obtain 1-chlorooctane (V) (100 g). 100 g of the 1-chlorooctadecane (V), 200 g of chlorobenzene, 167 g of a 32% by weight sodium bisulfide solution in water and 4 g of tetra-butylammonium bromide are added into a 1000 ml four-necked flask with a stirrer, a thermometer and a condenser. At a temperature in the range of from 65 to 70° C., the mixture is reacted for 12 h. The mixture is separated into an aqueous layer and an organic layer. The organic layer is n-octanethiol (III) (196 g).

Example 3

Under nitrogen atmosphere, 100 g of chlorobenzene, 100 g of 2-chlorobenzonitrile (II), 154 g of n-dodecanethiol (III) and 4 g of tetra-butylammonium bromide are added into a 500 ml four-necked flask with a stirrer, a thermometer, a dropping funnel and a condenser. At a temperature in the range of from 65 to 70° C. according to step a), 98 g of a 32% by weight sodium hydroxide solution in water are added dropwise. After the completion of the dropwise addition, the mixture is further reacted for 4 hours. The mixture is separated into an aqueous layer and an organic layer. The organic layer comprises 2-(dodecylthio)benzonitrile (IV) (320 g).

According to step b) 320 g of the organic layer, comprising the 2-(dodecylthio)benzonitrile (IV) obtained in step a), 200 g of chlorobenzene and 30 g of water are added into a 1000 ml four-necked flask with a stirrer, a thermometer and a condenser. At a temperature in the range of from 20 to 30° C., 54 g chlorine are blown into the mixture over a period of 2 hours. The mixture is further heated to a temperature in the range of from 60 to 65° C. and then allowed to further react for 1 h. During the reaction the reaction mixture (RM) is formed. After completion of the reaction the reaction mixture (RM) is cooled to a temperature in the range of from 20 to 30° C. and according to step c) 200 g of water are added to the reaction mixture (RM). A 32% by weight sodium hydroxide solution is added dropwise to the reaction mixture (RM) to give a pH-value in the range of from 9 to 10. The mixture is heated to a temperature in the range of from 60 to 65° C. and according to step d) separated into a first phase and a second phase. The first phase is cooled to a temperature in the range of from 20 to 30° C. A 31% by weight hydrochloric acid solution is added dropwise to the first phase to give a pH-value in the range of from 3 to 4. Crystals of 1,2-benzisothiazolin-3-one (I) precipitate. The precipitated crystals are collected by filtration, washed with water, and dried to obtain 1,2-benzisothiazolin-3-one (I) (100 g, HPLC>99%), the yield to 2-chlorobenzonitrile (II) is 91.7%.

The second phase (450 g) is distilled to obtain 1-chlorododecane (V) (145 g). 145 g of the 1-chlorododecane (V), 100 g of chlorobenzene, 160 g of a 32% by weight sodium bisulfide solution in water and 4 g of tetra-butylammonium bromide are added into a 1000 ml four-necked flask with a stirrer, a thermometer and a condenser. At a temperature in the range of from 65 to 70° C., the mixture is reacted for 12 h. The mixture is separated into an aqueous layer and an organic layer. The organic layer is n-dodecanethiol (III) (240 g).

Example 4

Under nitrogen atmosphere, 100 g of chlorobenzene, 100 g of 2-chlorobenzonitrile (II), 240 g of the n-dodecanethiol (III) obtained in example 3, 24 g of n-dodecanethiol (III) and 4 g of tetra-butylammonium bromide are added into a 500 ml four-necked flask with a stirrer, a thermometer, a dropping funnel and a condenser. At a temperature in the range of from 50 to 55° C. according to step a), 98 g of a 32% by weight sodium hydroxide solution in water are added dropwise. After the completion of the dropwise addition, the mixture is further reacted for 4 hours. The mixture is separated into an aqueous layer and an organic layer. The organic layer comprises 2-(dodecylthio)benzonitrile (IV) (315 g).

According to step b) 315 g of the organic layer, comprising the 2-(dodecylthio)benzonitrile (IV) obtained in step a), 200 g of chlorobenzene and 40 g of water are added into a 1000 ml four-necked flask with a stirrer, a thermometer and a condenser.

At a temperature in the range of from 20 to 30° C., 54 g chlorine are blown into the mixture over a period of 2 hours. The mixture is further heated to a temperature in the range of from 60 to 65° C. and then allowed to further react for 1 h. During the reaction the reaction mixture (RM) is formed. After completion of the reaction the reaction mixture (RM) is cooled to a temperature in the range of from 20 to 30° C. and according to step c) 200 g of water are added to the reaction mixture (RM). A 32% by weight sodium hydroxide solution is added dropwise to the reaction mixture (RM) to give a pH-value in the range of from 9 to 10. The mixture is heated to a temperature in the range of from 60 to 65° C. and according to step d) separated into a first phase and a second phase. The first phase is cooled to a temperature in the range of from 20 to 30° C. A 31% by weight hydrochloric acid solution is added dropwise to the first phase to give a pH-value in the range of from 3 to 4. Crystals of 1,2-benzisothiazolin-3-one (I) precipitate. The precipitated crystals are collected by filtration, washed with water, and dried to obtain 1,2-benzisothiazolin-3-one (I) (101 g, HPLC>99%), the yield to 2-chlorobenzonitrile (II) is 92.7%.

The second phase (450 g) is distilled to obtain 1-chlorododecane (V) (148 g). 148 g of the n-chlorododecane (V), 100 g of chlorobenzene, 160 g of a 32% by weight sodium bisulfide solution in water and 4 g of tetra-butylammonium bromide are added into a 1000 ml four-necked flask with a stirrer, a thermometer and a condenser. At a temperature in the range of from 65 to 70° C., the mixture is reacted for 12 h. The mixture is separated into an aqueous layer and an organic layer. The organic layer is n-dodecanethiol (III) (241 g).

Example 5

Under nitrogen atmosphere, 100 g of chlorobenzene, 100 g of 2-chlorobenzonitrile (II), 154 g of n-dodecanethiol (III) and 4 g of tetra-2-butylammonium bromide are added into a 500 ml four-necked flask with a stirrer, a thermometer, a dropping funnel and a condenser. At a temperature in the range of from 65 to 70° C. according to step a), 98 g of a 32% by weight sodium hydroxide solution in water are added dropwise. After the completion of the dropwise addition, the mixture is further reacted for 4 hours. The mixture is separated into an aqueous layer and an organic layer. The organic layer comprises 2-(dodecylthio)benzonitrile (IV) (320 g).

According to step b) 320 g of the organic layer, comprising the 2-(dodecylthio)benzonitrile (IV) obtained in step a), 200 g of chlorobenzene and 30 g of water are added into a 1000 ml four-necked flask with a stirrer, a thermometer and a condenser. At a temperature in the range of from 20 to 30° C., 100 g sulfuryl chloride are added dropwise to the mixture over a period of 2 hours. The mixture is further heated to a temperature in the range of from 60 to 65° C. and then allowed to further react for 1 h. During the reaction the reaction mixture (RM) is formed. After completion of the reaction the reaction mixture (RM) is cooled to a temperature in the range of from 20 to 30° C. and according to step c) 200 g of water are added to the reaction mixture (RM). A 32% by weight sodium hydroxide solution is added dropwise to the reaction mixture (RM) to give a pH-value in the range of from 9 to 10. The mixture is heated to a temperature in the range of from 60 to 65° C. and according to step d) separated into a first phase and a second phase. The first phase is cooled to a temperature in the range of from 20 to 30° C. A 31% by weight hydrochloric acid solution is added dropwise to the first phase to give a pH-value in the range of from 3 to 4. Crystals of 1,2-benzisothiazolin-3-one (I) precipitate. The precipitated crystals are collected by filtration, washed with water, and dried to obtain 1,2-benzisothiazolin-3-one (I) (106 g, HPLC>99%), the yield to 2-chlorobenzonitrile (II) is 97.2%.

The second phase (445 g) is distilled to obtain n-chlorododecane (V) (143 g). 143 g of the n-chlorododecane (V), 100 g of chlorobenzene, 180 g of a 32% by weight sodium bisulfide solution in water and 4 g of tetra-butylammonium bromide are added into a 1000 ml four-necked flask with a stirrer, a thermometer and a condenser. At a temperature in the range of from 65 to 70° C., the mixture is reacted for 12 h. The mixture is separated into an aqueous layer and an organic layer. The organic layer is n-dodecanethiol (III) (244 g).

The invention claimed is:
1. A method for producing a 1,2-benzisothiazolin-3-one compound of formula (I)

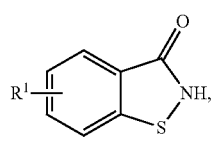

wherein
$R^1$ is selected from the group consisting of hydrogen, unsubstituted or at least monosubstituted $C_1$-$C_{10}$-alkyl, $OR^2$, $C(O)OR^2$, F, Cl, Br, I and $NO_2$, wherein the substituents are selected from the group consisting of F, Cl, Br, I, OH, $NH_2$ and $C_5$-$C_{10}$-aryl,
wherein
$R^2$ is selected from the group consisting of hydrogen, unsubstituted or at least monosubstituted $C_1$-$C_{10}$-alkyl and unsubstituted or at least monosubstituted $C_5$-$C_{10}$-aryl,
wherein the substituents are selected from the group consisting of F, Cl, Br, I, OH, $NH_2$, $C_1$-$C_{10}$-alkyl and $C_5$-$C_{10}$-aryl;
comprising the steps
a) reacting a 2-halobenzonitrile compound of formula (II)

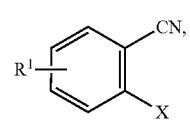

wherein
X is selected from the group consisting of F, Cl, Br and I;
with a thiol compound of formula (III)

wherein
$R^3$ is selected from the group consisting of unsubstituted or at least monosubstituted $C_8$-$C_{30}$-alkyl, unsubstituted or at least monosubstituted $C_5$-$C_{30}$-aryl and unsubstituted or at least monosubstituted $C_6$-$C_{30}$-aralkyl,
wherein the substituents are selected from the group consisting of F, Cl, Br, I, OH, $NH_2$, $C_1$-$C_{10}$-alkyl and $OR^4$,
wherein
$R^4$ is hydrogen or $C_1$-$C_{10}$-alkyl;
in the presence of at least one base (B) to form an intermediate of formula (IV)

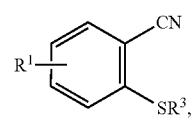

and
b) reacting the intermediate of formula (IV) obtained in step a) with a halogenation agent in the presence of water to form a reaction mixture (RM), comprising the 1,2-benzisothiazolin-3-one of formula (I) and a halide compound of formula (V)

wherein
$X^1$ is Cl or Br.
2. The method according to claim 1, wherein in step b) the halogenation agent is selected from the group consisting of chlorine, bromine, sulfuryl chloride and sulfuryl bromide.
3. The method according to claim 1, wherein step b) is carried out in the presence of an organic solvent and the organic solvent is selected from the group consisting of benzene, toluene, xylenes, aryl halides, $C_5$-$C_{14}$-alkanes, and alkyl halides.
4. The method according to claim 1, wherein step b) is followed by the following steps:
c) adding water and a second base (B2) to the reaction mixture (RM) obtained in step b) to give a first phase, comprising the 1,2-benzisothioazolin-3-one compound (I) and a second phase, comprising the halide compound (V), and d) separating the first phase from the second phase.

5. The method according to claim 4, wherein step d) is followed by step e), in which the halide compound (V) comprised in the second phase is reacted with a sulfide compound to give a thiol compound (III).

6. The method according to claim 5, wherein the thiol compound (III) obtained in step e) is recycled to step a).

7. The method according to claim 1, wherein the base (B) and optionally the second base (B2) are independent of each other selected from the group consisting of metal hydroxides, metal carbonates and metal alkoholates.

8. The method according to claim 5, wherein the sulfide compound in step e) is selected from the group consisting of thiourea, a metal bisulfide and a metal sulfide.

9. The method according to claim 4, wherein step c) is carried out in the presence of a heterogeneous solvent system, comprising an aqueous solvent and an organic solvent.

10. The method according to claim 1, wherein step a) is carried out in the presence of a heterogeneous solvent system, comprising an aqueous solvent and an organic solvent.

11. The method according to claim 10, wherein the organic solvent comprised in the heterogeneous solvent system in step a) is selected from the group consisting of benzene, toluene, xylenes, aryl halides and $C_5$-$C_{14}$-alkanes.

12. The method according to claim 10, wherein step a) is carried out in the presence of at least one phase transfer catalyst selected from the group consisting of quaternary ammonium salts, quaternary phosphonium salts and crown ethers.

13. The method according to claim 1, wherein step a) is carried out in the presence of a homogeneous solvent system, comprising at least one polar aprotic solvent.

\* \* \* \* \*